United States Patent [19]

Amoils

[11] Patent Number: 5,649,943

[45] Date of Patent: Jul. 22, 1997

[54] OPHTHALMIC TREATMENT APPARATUS AND ITS USE

[76] Inventor: Percy Amoils, P.O. Box 651510, Benmore 2010, South Africa

[21] Appl. No.: 456,604

[22] Filed: Jun. 1, 1995

[30] Foreign Application Priority Data

| Jun. 15, 1994 | [ZA] | South Africa | 94/4220 |
| Dec. 9, 1994 | [ZA] | South Africa | 94/9828 |

[51] Int. Cl.$^6$ ...................................................... A61B 17/24
[52] U.S. Cl. ............................ 606/161; 606/5; 606/107; 606/166
[58] Field of Search ................... 606/4, 5, 107, 606/161, 166, 180; 433/125, 166; 15/22.1

[56] References Cited

U.S. PATENT DOCUMENTS

| 1,907,286 | 6/1933 | Chott | 433/166 |
| 3,939,599 | 2/1976 | Henry et al. | 433/125 |
| 4,834,748 | 5/1989 | McDonald | 606/166 |
| 5,120,225 | 6/1992 | Amit | 15/22.1 |
| 5,269,795 | 12/1993 | Arnott | 606/166 |
| 5,482,461 | 1/1996 | Yale | 433/125 |
| 5,498,159 | 3/1996 | Coss | 433/125 |
| 5,504,961 | 4/1996 | Yang | 15/22.1 |

*Primary Examiner*—Michael Buiz
*Assistant Examiner*—Mark S. Leonardo
*Attorney, Agent, or Firm*—Rines and Rines

[57] ABSTRACT

An ophthalmic method and apparatus preferably for removing the relatively soft cellular epithelium from a predetermined region of the relatively hard fibrous cornea of the eye preparatory to reshaping the cornea as by laser ablation or the like, preferably by an abrasive surface formed by the ends of a bundle of thin soft filaments constrained against lateral movement and rotatable to comminute and emulsify the epithelium into tiny removable cell-particles, with features, where desired, of concavely contouring the surface formed by the free ends of the filaments to correspond to the anterior convex cornea, and interiorly hollowing the bundle to provide an annular abrasive surface formed by filament ends surrounding the hollow.

32 Claims, 2 Drawing Sheets

OPHTHALMIC TREATMENT APPARATUS AND ITS USE

FIELD OF THE INVENTION

This invention relates to ophthalmic apparatus for use in removing superficial epithelium of the eye cornea preparatory to carrying out surgery on the eye, in particular, a photo-refractive keratectomy, as by excimer laser ablation or the like, and to a method of using such apparatus for such purpose.

BACKGROUND TO INVENTION

Photo-refractive keratectomy is fast becoming a popular surgical method of correcting sight disorders by removing a thin disc shaped layer of tissue in the center of the cornea using a laser beam which creates a new contour to the lens surface. Differing thicknesses of tissue are removed by causing the diameter of the laser beam to change, generally, from an initial central narrow beam, to a broader beam so that a lens shaped dish of tissue material is removed. Not only can myopia and hypermetropia or hyperopia be cured but also other defects such as astigmatism. (See, for example, The Excimer, Fundamentals and Clinical Use, Harold A. Stein et al, Slack Inc. 1994, pages 9–16).

In order to prepare an eye for such surgery it is necessary to remove the superficial cellular epithelium to expose the Bowman's layer of the predetermined region(s) of the cornea to be reshaped. Great care must be taken not to damage the subjacent Bowman's layer of the fibrous cornea.

Heretofore this superficial epithelium has been removed either by weakening the epithelium with alcohol, and then scratching away the soft tissue or alternatively, by scraping the epithelium using a sterile, spatulated scalpel.

Alcohol, however, has a tendency to cause slight swelling of the cornea which can prevent an accurate result from being achieved.

The spatula method, on the other hand, is a rather difficult technique and often causes damage to the underlying Bowman's layer or, more commonly, does not completely remove the epithelial layer. Small tags of epithelium remaining can result in uneven laser ablation.

It has also recently been proposed to use a rotatable brush of non-contiguous separated plastic self-supporting tapered pins, as derived from surgical hand scrubbing brushes, and to attach the same in line with a hand-held housing carrying a longitudinal rotating shaft. The surgeon applies the brush to the central area of the cornea causing the rotating pins to tear or rip away within 2–3 seconds the central portion of the epithelium—with the torn off epithelium caught between the pins for removal, as described in an article entitled "Rotating Brush for Fast Removal of Corneal Epithelium" by I. G. Pallikares et al, appearing in the Journal of Refractive & Corneal Surgery, Vol. 10, July/August 1994, pages 438–442.

While suggesting an important conceptual direction, this construction, however, introduces serious disadvantages including view-destruction by the presence during use of the longitudinal hand-held housing rearward of the brush, difficulty fitting, adjusting, tilting and operating in the limited space between the objective of the surgeon's operating microscope and patient's eye, and the resulting rough epithelial edges left by the torn off central epithelium portion.

OBJECT OF THE INVENTION

It is the object of this invention, therefore, to provide a new and improved ophthalmic treatment apparatus and a method of its use whereby the epithelial layer can be more faciley and accurately, cleanly and effectively removed preparatory to surgery; in particular, but not exclusively using a laser ablation beam, and that shall not be subject to any of the above-described difficulties.

Other and further objects will be explained hereinafter and more particularly delineated in the appended claims.

SUMMARY OF THE INVENTION

From one of its broader viewpoints, the invention embraces a method of ophthalmic treatment involving removing the relatively soft cellular epithelium of a predetermined region of the anteriorly convexly curved relatively hard fibrous cornea of an eye preliminary to reshaping the cornea as by laser ablation, that comprises, forming an abrasion surface of concave curvature corresponding substantially to the convex curvature of the cornea at said predetermined region; lightly applying the abrasive surface to said predetermined region of the cornea with the surface and cornea in substantially curved parallel juxtaposition; and rotating said abrasive surface to comminute-emulsify the said epithelium of the cornea into tiny removable cell particles.

In accordance with this invention, there is provided ophthalmic treatment apparatus comprising a scarifier member rotatable about an axis and having an operative abrasive surface of substantially part-spherical, concave shape with the concavity curvature being substantially complementary to and corresponding substantially to the convex curvature or shape of the outer surface or anterior of an eye cornea, and wherein the abrasive nature of the surface is adapted to effect substantial loosening by comminuting and emulsifying of the multi-layer relatively soft cellular epithelium, of an eye, preferably comminuting the cells into tiny particles, without damage to the subjacent Bowman's layer of the relatively hard fibrous abrasion-resistant cornea layers.

Further features of the invention provide for the abrasive surface to be defined by the ends of a multitude of a tightly packed bundle of contiguous fine non-self-supporting filaments or bristles of a circular brush and wherein the bristles are preferably of thin synthetic plastic material, and of a nature enabling them to be adequately sterilized; for the bristles to be supportively held in close contiguous proximity to each other and preferably, though not always essentially, particularly if very short, to be restricted from lateral movement by a surrounding collar which is preferably longitudinally adjustable along the length of the bristles to enable the flare and/or length thereof to be varied and thus the effective stiffness and/or abrasiveness of the bristle ends to be adjusted. In some instances, later detailed, the abrasive surface may be of annular shape in end view (i.e. with a longitudinal hollow such as a central void in the mass of bristles).

The invention also provides a method of removing the superficial epithelium of an eye including the step of causing the concave abrasive surface of a scarifier member as defined above to rotate about its axis; and contacting said surface lightly with the epithelium of the eye to loosen by cellular comminution and emulsifying and enable same to be removed to a predetermined and controlled depth.

The scarifier member, as above stated, is preferably in the form of a brush having a multitude of contiguous synthetic plastic thin filament bristles made of a suitable material, such as that sold under the trade name TYNEX by DUPONT Inc., and densely packed together to provide a substantially continuous abrasive surface at the free end of the brush. The radius of curvature of the abrasive surface formed by the free ends of the tightly packed bundle of filaments is generally formed to be about 7 mm, and the concave surface corresponds to that of a sphere having a diameter of about 14 mm for the cornea reshaping purposes herein described. The circular brush, moreover, as before mentioned, may have an intermediate hollow or void such as a central region devoid of bristles, thus defining an annular abrasive surface in end view—particularly useful for removing peripheral regions of the epithelium as later discussed.

It has been found that a modified rotatable toothbrush of the type sold under the trade name ROTADENT by Professional Dental Technologies Inc. may be adapted to the very different purposes of the invention, wherein the ends of the bristles are trimmed to provide the appropriate concave surface, such, indeed, having proven to be ideal for the purpose of the invention. Indeed, so too is the battery powered, hand-operated toothbrush holder ideal for rotating the scarifier member of the invention. The bristles are held in their normal parallel relationship but in a manner to prevent them from bending outwardly to any undesirable extent, by means of a collar which surrounds the bristles and which is made adjustable in position axially along the length of the bristles to adjust the length and flare of bristle extending beyond the collar. Accordingly, the effective hardness or stiffness and abrasiveness of the concave surface defined by the bristle free ends may be faciley so adjusted.

Trimming of the bristle ends to provide the concave surface can be easily achieved by locating a prefabricated brush in a jig, rotating the jig, and with the aid of an abrasive element or paper held to a suitable spherical or arcuate shape, forming the concave plane defined by the bristle ends. It is also possible that the bristles may be made to a much shorter length, and to a fixed degree of hardness, to thereby obviate in some cases the necessity of employing a collar.

Preferred and best mode embodiments are hereinafter detailed.

In order that the invention may be more fully understood, a preferred embodiment thereof will now be described with reference to the accompanying drawings.

DETAILED DESCRIPTION WITH REFERENCE TO THE DRAWINGS

Figure 1:
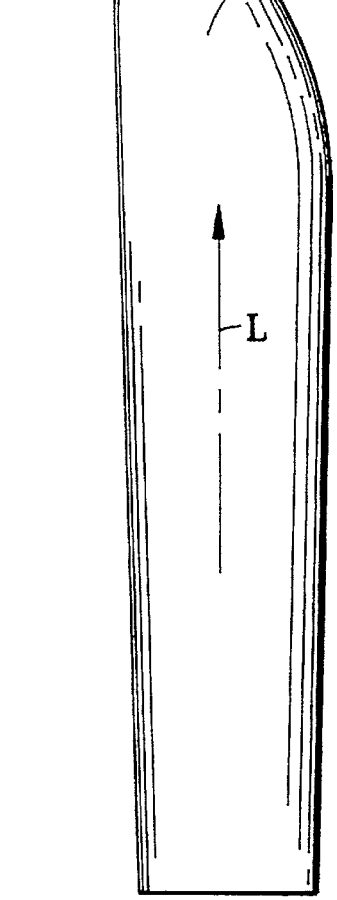
FIG. 1 illustrates a modified electric toothbrush assembly of a type fortuitously suitable for the very different use in implementing this invention, shown vertically oriented, but in practice usually horizontally held over a patient in a lying-down posture.

In this preferred embodiment of the invention, a scarifier member, generally indicated by numeral 1, assumes a modified form of a substantially conventional rotatable cylindrical toothbrush having a diameter of about 7 mm. The brush is adapted to be driven with its axis extending transversely at right angles to the longitudinal axis of a handle containing a battery powered toothbrush drive assembly 2, the brush being mounted at the upper end of the handle, as shown in FIG. 1, projecting a short distance transversely thereto.

The scarifier member of the invention has a base 3 from which a multitude of parallel tightly bundled contiguous thin filament bristles 4 extend. Conveniently the bristles have a length of about 8 mm and a diameter of about 80 to 100 µm. As before mentioned, bristles are preferably made of, in this case, a monofilament sold under the name of TYNEX by DUPONT Inc. This material can be sterilized by chemical methods, thereby avoiding any loss of shape which may be occasioned by autoclaving or other thermal sterilization.

Figure 3:
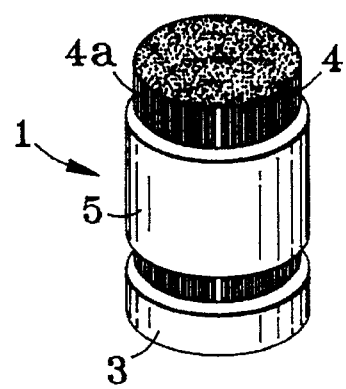
FIG. 3 illustrates, in isometric view, a complete scarifier member in enlarged view.
Figure 5:
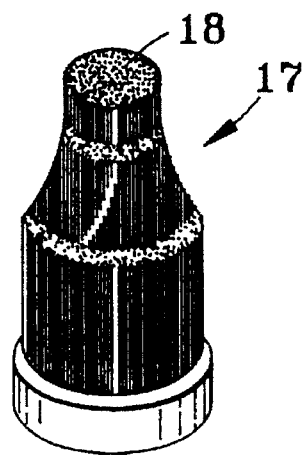
FIGS. 5 & 6 illustrate, in section, two different collars for use on the scarifier members.
Figure 6:
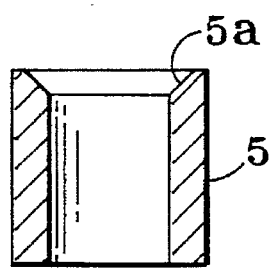

The bristles are held in a confined juxtaposed bundled relationship, as shown most clearly in FIG. 3, preferably by an external collar 5. The collar can be adjusted in position along the length of the bristles to adjust the rigidity of the portion 4a of the bristles and the free ends thereof extending beyond the collar. Also as shown in FIG. 5, the inner edge 5a of the collar may be beveled to allow a limited amount of flare of the bristles, or, as shown in FIG. 6, the inner edge could be stepped as indicated by numeral 5b.

The employment of the compacted tight bundle of soft contiguous filaments, each preferably of the order of the before-mentioned 80 microns (two human hair in diameter) as of TYNEX® filaments, has been found to lend itself to the convenient bundle/encasement and confinement by the circular binding collar or sleeve 5. As earlier explained, the collar 5 may be slidable or otherwise adjustable to allow a variable of flare and/or length of exposed filaments and variable stiffness and abrasion characteristics, with the filaments held against substantial lateral movement or spreading (as of course, occurs with the very different circumstance of toothbrushing) to insure abrasion confinement to the desired epithelmic region only, for dearly and accurately removing the corneal epithelium prior to the before-mentioned excimer laser surgery. Following the laser treatment, a new epithelium layer grows over and protects the reshaped cornea.

Figure 2A:
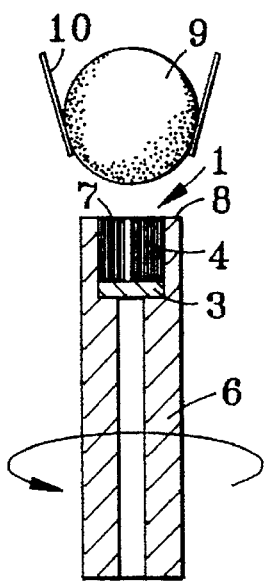
FIGS. 2a & 2b illustrate two steps in the formation of the required scarifier member according to the required scarifier member according to the invention by a manual method.

In order, for the purposes of this invention, to provide the required part-spherical concave abrasive plane surface defined by the bristle free ends, as before discussed, an appropriate conventional toothbrush-like assembly may be located in a jig 6, FIG. 2a, which confines the bristles to extend substantially parallel to the axis of the jig. The jig receives the entire brush such that the ends 7 of the bristles are substantially flush with the end 8 of the jig.

The jig, as before described, is rotated and the ends 7 of the bristles are contacted by an abrasive spherical or circular element 9 which can conveniently be a suitable diameter metal ball having an abrasive surface; in this case, provided by a strip of sandpaper held over the arcuate surface of the ball.

Figure 2B:
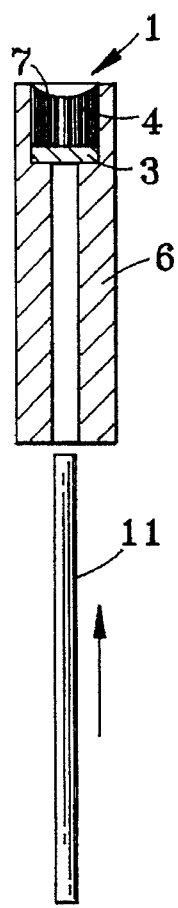

The result is shown in FIG. 2b where the ends 7 of the bristle have been trimmed to provide a substantially spherical dish-shaped concave abrasive surface, the radius of curvature of the dish being adjusted to about 7 mm to conform well to the average shape of an eye, which has a radius in the corneal zone of between 7.2 and 8.2 mm.

In order to remove the brush from the jig, FIG. 2b, a rod or stick 11 can be slid up a bore through the jig to force the brush out of the jig cavity. The collar 5 can then be installed in position, as in FIG. 3.

In order to remove the epithelium from the desired predetermined region of the cornea of an eye, as indicated by numeral 13 in FIG. 1, the scarifying brush member 1 above-described is fitted to the upper end (as shown in FIG. 1) of the motor handle 2, projecting transversely (T) to the handle longitudinal axis (L). The surgeon grasps the longitudinal handle 2 and holds it say horizontally under the operating microscope M and above the patient's eye 13, though shown in vertical position in FIG. 1. The member 1 is applied by the surgeon moving the horizontally held handle vertically-downward toward the eye and lightly contacting the concavely contour brush ends with the corresponding convexly curved parallel juxtaposed cornea 14 of the eye in the required region or position which can be premarked by the ophthalmic surgeon. The surgeon operates the motor button 2' to set the brush into abrading rotation, periodically or successively, applying, removing by lifting, checking and re-applying as needed to comminute and emulsify into tiny particles all of the epithelium cells over the exact predetermined region marked out for removal, wiping and/or washing the fine particles away as required. The predetermined region is then ready for the laser ablation procedure.

It has been found that, in practice, use of the apparatus described above and in the manner explained, effectively removes the epithelium without damaging the Bowman's membrane of the fibrous cornea and in a much simpler, safer, cleaner, controlled and efficacious manner than the methods used heretofore. Since the cornea under the epithelium is fibrous and abrasion resistant, the abrasion is automatically limited to the softer epithelium cells alone, with the brush leaving the cornea untouched.

It has been found, in accordance with the discovery underlying the present invention, that, contrary to the above-described earlier rotating brush operation for corneal epithelium removal of the above-cited article, a remarkably clean, smooth, accurate and controlled-area epithelium removal can be achieved if the epithelium is not torn but rather its cells are comminuted and somewhat emulsified, into tiny particles, by the rotating action of the rotary scrubber or brush 1 of the invention with its tight bundle of contiguous fine filament bristles. With the brush mounting transversely offset from an end region of the longitudinal handle 2 (preferably at the before-described substantially right angles), the surgeon has an unobstructed view at all times of the position and effect of the brush in action as the longitudinal handle is transversely vertically moved and applied to and from the cornea. Repeated application with wiping or washing as with BSS solution, insures removal of epithelium over the total desired predetermined region of the cornea, clearing away the exact area and shape thereof to be treated by the laser.

Figure 4:
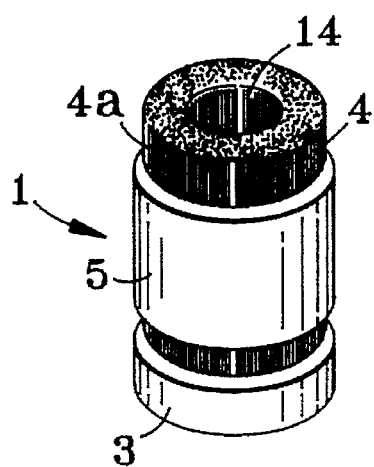
FIG. 4 is a view similar to FIG. 3 but of a brush having a central void.

A modified brush scarifying member is illustrated in FIG. 4 where a central void 14 is formed in the center of the member so that the abrasive brush end surface is annular in end view and thus permits accommodation for slightly different dimensions of radius of curvature of the cornea. This has the advantage that the more resistant peripheral epithelium regions can be removed first followed by removal of the central zone by simply contacting and wiping the periphery of the scarifying member therewith, thus not always requiring the total concave curvature of the assembly of brush ends.

With a brush about 7 mm diameter corresponding to the usual circular region diameter of the cornea to be treated, the hollow or void 14 is shown in FIG. 4, as an example, as of diameter in about the 2 mm range.

Figure 7:
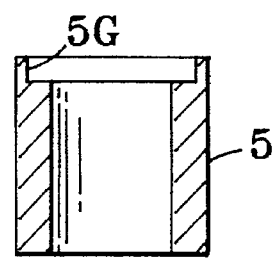
FIG. 7 illustrates a special scarifier member for use in extending the area of epithelium removal.
Figure 8:
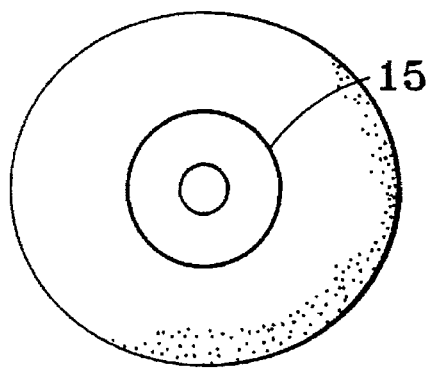
FIGS. 8 & 9 illustrate schematically the area of epithelium removal for two different types of corrective treatment.
Figure 9:
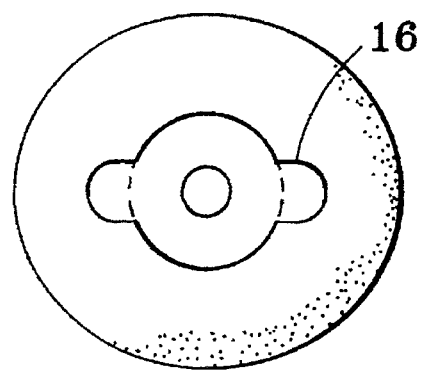

The usual shape of the removed area of epithelium is circular as shown by numeral 15 in FIG. 8, in the case of correcting myopia or hypermetropia. In the case of correcting an astigmatism the usual circular area of about 7 mm diameter must be extended laterally on each side by an area about 4 mm wide to provide an overall removal area of about 9 mm long as indicated by numeral 16 in FIG. 9. A scarifier 17 having an abrasive surface 18 of about 3 mm in diameter can be used to form the extensions (see FIG. 7).

It will be understood that numerous variations may be made to the embodiments of the invention described above without departing from the scope hereof. In particular, the scarifying member may have an abrasive surface defined by material other than bristle ends. In particular it is envisaged that a solid concave surface having an abrasive facing could be employed. Such abrasive facing could be formed of any suitable material such as, for example, sintered metal particles bonded to a metal base or any other suitable abrasive metal.

Also, the collar may be omitted if the bristles are made sufficiently short so that they are self-confined and do not splay outwardly to a deleterious extent. In this case, adjustment of the rigidity of the projecting ends of the bristles would not be possible but it is envisaged, in that case, that different lengths or different stiffnesses of bristles could be used.

It is also to be understood that the invention may also be applied more generally to other similar tissue or in other applications where an abradable relatively soft layer is to be accurately removed from an underlying harder and more abrasion-resistant surface. Further modifications will also suggest themselves to those skilled in this art, and such are considered to fall within the spirit and scope of the invention as defined in the appended claims.

What is claimed is:

1. A method of ophthalmic treatment involving removing a relatively soft cellular epithelium of a predetermined region of an anteriorly convexly curved relatively hard fibrous cornea of an eye preliminary to reshaping the cornea as by laser ablation, that comprises, forming an abrasive surface of concave curvature corresponding substantially to the convex curvature of the cornea at said predetermined region; lightly applying the abrasive surface to said predetermined region of the cornea with the surface and cornea in substantially curved parallel juxtaposition; and rotating said abrasive surface to comminute-emulsify the said epithelium of the cornea into tiny removable cell particles, and in which the abrasive surface is formed by a tight bundle of contiguous fine filament brush bristles having free ends, the bundle of such free ends being shaped transversely to define said concave curvature.

2. A method as claimed in claim 1 and in which, during successive applying to effect such comminuting, the particles are removed by wiping or washing the same away.

3. A method as claimed in claim 1 and in which a longitudinal hollow is provided within the bundle of filament bristles to form an annular abrasive surface.

4. A method as claimed in claim 1 and in which the bundle is intermediately confined to restrain lateral movement of the filament bristles.

5. A method as claimed in claim 1 and in which the brush bristles have flare, length, stiffness and abrasiveness characteristics, and one of the flare of said free ends, the bristle length, and the degree of stiffness and abrasiveness of the bristles is varied.

6. A method as claimed in claim 5 and in which the variation is effected by collaring the bundle at different locations therealong.

7. Ophthalmic treatment apparatus for removing the relatively soft cellular epithelium of a predetermined region of the anteriorly convexly curved relatively hard fibrous cornea of the eye preliminary to reshaping the cornea as by laser ablation, said apparatus having, in combination, a scarifier rotatable about an axis and provided with an operative abrasive surface of substantially part-spherical concave curvature substantially complimentary and corresponding to the convex curvature of said predetermined region of the cornea; and a motor drive for rotating the scarifier when the abrasive surface is applied lightly against and substantially parallel to the said predetermined region of the cornea, and in which the scarifier abrasive surface is formed and defined by a multitude of tightly bundled contiguous fine filament bristles, having free ends, such a bundle of free ends being shaped to define said concave curvature, and in which the bristles are constrained in a tight bundle by a surrounding collar.

8. Apparatus as claimed in claim 7 and in which the collar is longitudinally adjustable along the length of the bristles to permit variation of free end flare, bristle length and the degree of stiffness and abrasiveness.

9. Apparatus as claimed in claim 7 and in which the collar is provided with one of a beveled or stripped edge.

10. Apparatus as claimed in claim 7 and in which the bundled bristles are intermediately provided with a hollow devoid of filaments to provide an annular scarifier brush.

11. A method of ophthalmic treatment involving removing a relatively soft cellular epithelium of a predetermined region of an anteriorly convexly curved relatively hard fibrous cornea of an eye preliminary to reshaping the cornea as by laser ablation, that comprises, forming an abrasive surface of concave curvature corresponding substantially to the convex curvature of the cornea at said predetermined region; lightly applying the abrasive surface to said predetermined region of the cornea with the surface and cornea in substantially curved parallel juxtaposition; and rotating said abrasive surface to comminute-emulsify the said epithelium of the cornea into tiny removable cell particles, and in which the abrasive surface is mounted to project transversely of an end of a longitudinal motor drive housing serving also or an operating longitudinal-axis handle; and in which the abrasive surface is formed of a tight bundle of contiguous fine filament brush bristles, the bundle having free ends transversely shaped to define said concave curvature, and the applying and comminuting-emulsifying is effected as the longitudinal handle is moved transversely at substantially right angles to the handle axis against the cornea, and with a continuous open view of such applying to the cornea unobstructed by the handle or its operation.

12. A rotatable ophthalmic scarifier brush for the removal of a relatively soft cellular epithelium of a predetermined region of an anteriorly convexly curved relatively hard fibrous cornea of an eye preliminary to reshaping the cornea, having, in combination, a rotatable base holding a bundle of contiguous thin filament bristles projecting therefrom, and an intermediate collar disposed about the bundle and confining the filament bristles into a tightly packed bundle restrained from lateral movement, and in which a hollow is provided within the bundle to form an annular brush.

13. A rotatable ophthalmic scarifier brush as claimed in claim 12 and in which the hollow provided within the bundle is of diameter in about the 2 mm range.

14. A rotatable ophthalmic scarifier brush for the removal of a relatively soft layer at a predetermined region of a relatively hard surface of predetermined contour having, in combinations a rotatable base holding a bundle of contiguous thin filament bristles projecting therefrom, an intermediate collar disposed about the bundle and confining the filament bristles into a tightly packed bundle restrained in lateral movement, and in which the said layer is a relatively soft cellular epithelium layer of a cornea, and the relatively hard surface is the relatively hard fibrous cornea thereunder.

15. A rotatable ophthalmic scarifier brush as claimed in claim 14 and in which the bristles have free ends shaped into a concave surface.

16. A rotatable ophthalmic scarifier brush as claimed in claim 15 and in which the concave surface is formed to correspond substantially to the anterior convex contour of the said predetermined region of the cornea.

17. A rotatable ophthalmic scarifier brush as claimed in claim 16 and in which the radius of curvature of said concave surface and the diameter of the brush are each about 7 mm.

18. A method of ophthalmic treatment involving removing a relatively soft cellular epithelium of one or more predetermined regions of an anteriorly convexly curved relatively hard fibrous cornea of an eye preliminary to reshaping the cornea as by laser ablation, that comprises, forming an abrasive surface with a hollow therein to define thereabout an effective abrasive annulus corresponding substantially to at least an annular portion of one or more of such region(s); lightly applying the abrasive surface to such region(s) of the cornea; rotating said abrasive annulus to comminute-emulsify the said epithelium at such region(s) into tiny removable cell particles.

19. A method of ophthalmic treatment involving removing a relatively soft cellular epithelium of one or more predetermined regions of an anteriorly convexly curved relatively hard fibrous cornea of an eye preliminary to reshaping the cornea as by laser ablation, that comprises, forming an abrasive surface of free ends of a bundle of contiguous fine filament bristles; intermediately confining the bundle to restrain lateral movement of the filament bristles; lightly applying the free ends to such predetermined region(s); and rotating the bundle of confined bristles to comminute-emulsify the said epithelium there at into tiny removable cell particles.

20. A method as claimed in claim 19 and in which the applying is effected intermittently successively until the epithelium cells over the complete predetermined region have been totally removed.

21. A method as claimed in claim 19 and in which the comminuted-emulsified particles are wiped or washed away after the abrasion.

22. A method as claimed in claim 19 and in which a hollow is formed in the bundle to define an effective abrasive annulus of bristle free ends.

23. A method as claimed in claim 22 and in which, after a corresponding annulus of corneal epithelium cells has been abraded, the bristle ends are then wiped across other of the predetermined regions, including central region(s) of the cornea, and rotated to comminute-emulsify the epithelium into tiny removable cell particles at such other regions also.

24. A method as claimed in claim 19 and in which the surface defined by the bristle free ends is concavely shaped.

25. A method of removing a relatively soft layer predetermined region of a relatively hard surface of predetermined contour that comprises, forming an abrasive surface of free ends of a bundle of contiguous fine filament bristles; confining the bundle to restrain lateral movement of the filament bristles; lightly applying the free ends to such predetermined region only; and rotating the bundle of confined bristles to comminute the said soft layer into removable particles accurately to expose said relatively hard surface there at without abrading said hard surface.

26. A method as claimed in claim 25 and in which the surface defined by the said free ends is shaped to correspond to the contour of the said hard surface along said predetermined region.

27. A method as claimed in claim 25 and in which the bundle is hollowed to provide an annular ring of filament bristle free ends.

28. A rotatable scarifier brush for the removal of a relatively soft layer at a predetermined region of a relatively hard surface of predetermined contour having, in combination, a rotatable base holding a bundle of contiguous thin filament bristles projecting therefrom, an intermediate collar disposed about the bundle and confining the filament bristles into a tightly packed bundle restrained from lateral movement, and in which a hollow is provided within the bundle to form an annular brush.

29. A rotatable scarifier brush as claimed in claim 28 and in which free ends of the bristles are shaped to correspond to said contour.

30. A rotatable scarifier brush for the removal of a relatively soft layer at a predetermined region of a relatively hard surface of predetermined contour having, in combination, a rotatable base holding a bundle of contiguous thin filament bristles projecting therefrom, an intermediate collar disposed about the bundle and confining the filament bristles into a tightly packed bundle restrained from lateral movement, and in which the filament bristles are each of the order of 80 microns in diameter.

31. A rotatable scarifier brush as claimed in claim 14 and in which the brush is attachable to the end of a handle having a motor drive for rotating the rotatable base of the brush.

32. A rotatable scarifier brush as claimed in claim 31 and in which the brush is attached to extend transversely to the handle at said end.

\* \* \* \* \*